(12) United States Patent
Pellegrino

(10) Patent No.: US 10,952,771 B2
(45) Date of Patent: Mar. 23, 2021

(54) VERTEBRAL ABLATION SYSTEM

(71) Applicant: K2M, Inc., Leesburg, VA (US)

(72) Inventor: Richard Pellegrino, Leesburg, VA (US)

(73) Assignee: K2M, Inc., Leesburg, VA (US)

( * ) Notice: Subject to any disclaimer, the term of this patent is extended or adjusted under 35 U.S.C. 154(b) by 433 days.

(21) Appl. No.: 15/557,936

(22) PCT Filed: Mar. 7, 2016

(86) PCT No.: PCT/US2016/021185
§ 371 (c)(1),
(2) Date: Sep. 13, 2017

(87) PCT Pub. No.: WO2016/148954
PCT Pub. Date: Sep. 22, 2016

(65) Prior Publication Data
US 2018/0055539 A1 Mar. 1, 2018

Related U.S. Application Data

(60) Provisional application No. 62/133,340, filed on Mar. 14, 2015.

(51) Int. Cl.
*A61B 18/12* (2006.01)
*A61B 17/34* (2006.01)
(Continued)

(52) U.S. Cl.
CPC .......... *A61B 17/3472* (2013.01); *A61B 17/34* (2013.01); *A61B 17/70* (2013.01); *A61B 17/7032* (2013.01); *A61B 17/8805* (2013.01); *A61B 17/864* (2013.01); *A61B 17/8625* (2013.01); *A61B 18/14* (2013.01); *A61B 18/1477* (2013.01); *A61B 18/1815* (2013.01); *A61B 2017/320069* (2017.08);
(Continued)

(58) Field of Classification Search
CPC ..... A61B 17/34; A61B 17/3472; A61B 17/70; A61B 17/7032; A61B 17/8625; A61B 17/864; A61B 17/8805; A61B 18/14; A61B 18/1477; A61B 18/1815; A61B 2017/320069; A61B 2018/00339; A61B 2018/00565; A61B 2018/00577; A61B 2018/00821
See application file for complete search history.

(56) References Cited

U.S. PATENT DOCUMENTS 6,146,380 A 11/2000 Racz et al.
6,572,593 B1 6/2003 Daum
(Continued)

OTHER PUBLICATIONS

International Search Report dated Jul. 18, 2016 issued in PCT Application No. PCT/US16/21185.
(Continued)

*Primary Examiner* — Daniel W Fowler
(74) *Attorney, Agent, or Firm* — Lerner, David, Littenberg, Krumholz & Mentlik, LLP

(57) ABSTRACT

A system for augmenting spinal vertebrae utilizing a system that increases the bone density of adjacent vertebral bodies is disclosed. This system may be placed in the cranial and/or caudal end positions of the spinal construct to address potential adjacent level failure.

26 Claims, 4 Drawing Sheets

(51) Int. Cl.
  *A61B 17/70*   (2006.01)
  *A61B 17/88*   (2006.01)
  *A61B 17/32*   (2006.01)
  *A61B 18/00*   (2006.01)
  *A61B 18/14*   (2006.01)
  *A61B 17/86*   (2006.01)
  *A61B 18/18*   (2006.01)
  *A61M 25/00*   (2006.01)
  *A61M 25/01*   (2006.01)
  *A61M 25/06*   (2006.01)
  *A61N 7/02*   (2006.01)

(52) U.S. Cl.
  CPC ............... *A61B 2018/00339* (2013.01); *A61B 2018/00565* (2013.01); *A61B 2018/00577* (2013.01); *A61B 2018/00821* (2013.01); *A61M 25/007* (2013.01); *A61M 25/0102* (2013.01); *A61M 25/0136* (2013.01); *A61M 25/0662* (2013.01); *A61M 2025/0681* (2013.01); *A61M 2205/36* (2013.01); *A61N 7/02* (2013.01)

(56) References Cited

U.S. PATENT DOCUMENTS

| | | | |
|---|---|---|---|
| 6,592,559 B1 | 7/2003 | Pakter et al. | |
| 8,080,009 B2 | 12/2011 | Lee et al. | |
| 8,414,580 B2 | 4/2013 | Rioux et al. | |
| 8,425,507 B2 | 4/2013 | Pellegrino et al. | |
| 2002/0002372 A1* | 1/2002 | Jahns | A61B 18/1492 606/41 |
| 2006/0020313 A1* | 1/2006 | Eggers | A61B 18/04 607/103 |
| 2008/0033493 A1* | 2/2008 | Deckman | A61B 18/0218 607/3 |
| 2010/0324506 A1* | 12/2010 | Pellegrino | A61B 17/3472 604/272 |
| 2013/0324996 A1 | 12/2013 | Pellegrino et al. | |
| 2015/0045783 A1* | 2/2015 | Edidin | A61B 18/04 606/29 |
| 2016/0199112 A1* | 7/2016 | Kim | A61B 17/1655 606/304 |

OTHER PUBLICATIONS

Written Opinion of the International Searching Authority dated Jun. 21, 2016 issued in corresponding PCT Application No. PCT/US16/21185.

\* cited by examiner

VERTEBRAL ABLATION SYSTEM

RELATED APPLICATION

This application is a National Stage Entry of International Application Number PCT/US2016/021185, filed on Mar. 7, 2016, which claims the benefit of, and priority to, U.S. Provisional Patent Application No. 62/133,340, filed on Mar. 14, 2015, the entire contents of each of which are incorporated by reference herein.

TECHNICAL FIELD

The present disclosure relates generally to a vertebral ablation system, a method of ablating osseous tissue in a vertebral body; and a kit.

BACKGROUND

The spinal column is a complex system of bones and connective tissues that provide support for the human body and protection for the spinal cord and nerves. The adult spine is comprised of an upper and lower portion. The upper portion contains twenty-four discrete bones, which are subdivided into three areas including seven cervical vertebrae, twelve thoracic vertebrae and five lumbar vertebrae. The lower portion is comprised of the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases and types of injury, which restrict the range of motion of the spine or interfere with important elements of the nervous system. The problems include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis, or bone tissue thinning and loss of bone density.

Spinal fixation apparatuses are widely employed in surgical processes for correcting spinal injuries and diseases.

One growing trend seen post-surgical treatment of a patient's spine is the incidence of proximal junctional kyphosis (PJK), which is typically an adult spinal deformity surgical outcome if the lumbar lordosis and thoracic kyphosis are not properly restored post-surgery. PJK appears at or above the cranial-most thoracic level treated. Even though PJK most commonly occurs in the thoracic region of the spine, it can also occur in various spinal regions and may occur above or below the instrument levels and may impact the next adjacent level or two that is not instrumented. This type of failure is called adjacent level failure. Symptoms of PJK and adjacent level failure include pain, neurological deficit, ambulatory difficulty and poor maintenance of sagittal balance. For patients that present with these symptoms, often the only treatment is an additional surgery. The incidence rate of PJK, but may be upward of 50% of long construct, instrumented fusion cases.

What is needed is a treatment targeted to the instrumented levels, and/or adjacent vertebral level(s) from those that are instrumented thereby reducing the likelihood of PJK.

SUMMARY

The present application is directed to an ablation system comprising a needle having a handle and a cannula; a stylet; and a probe.

In an aspect, there is also disclosed a method for ablating osseous tissue in a vertebral body comprising: inserting a probe into a cannula positioned in a vertebral body; and applying energy from the probe into vertebral body to ablate the osseous tissue.

In another aspect, there is disclosed a kit for ablating a vertebral body comprising a screw having a cannula; and a probe.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figures 1A, 1B, 1C:
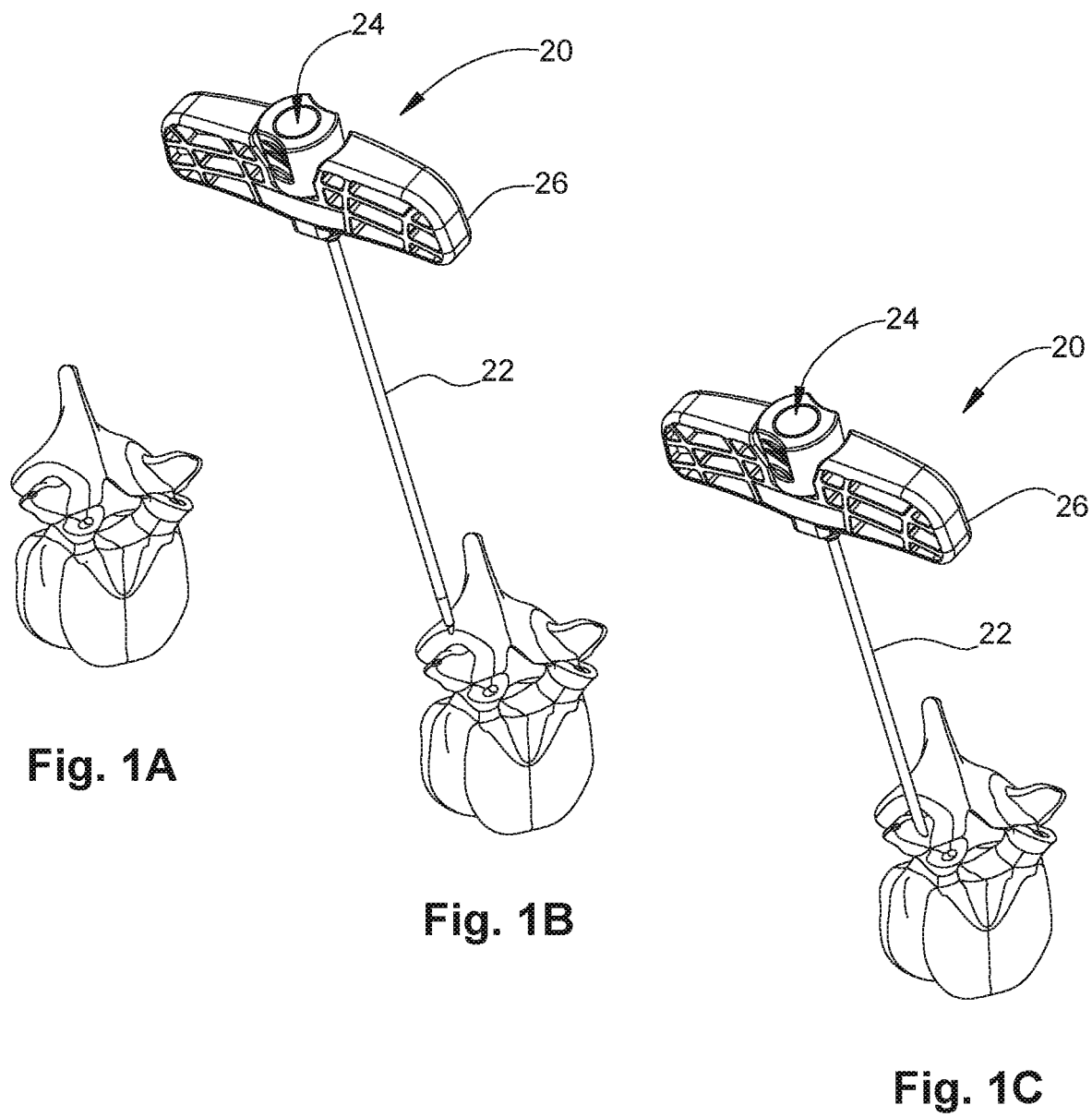
FIGS. 1A-1C show the steps of inserting a needle into a vertebral body.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Cranial refers to the spine segment closer to the head of the patient whereas caudal refers to the spine segment closer to the feet of the patient. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure is directed to an ablation system that can be used in a method of ablating osseous tissue in a vertebral body. In particular, the method can be targeted to an adjacent vertebral level(s) from those vertebral bodies that are instrumented. The ablation system can be used to ablate the osseous tissue, thereby creating a higher density bone portion within the vertebral body. It is expected that this higher density bone portion can sustain less load than the instrumented level, but more load than the typical non-instrumented level, thus reducing the likelihood of PJK in these adjacent levels. Additionally, this higher density bone portion can be used to offset the loading on the spine and provide a reduced stiffness to the construct.

The ablation system and its use are illustrated in the drawings. Referring to FIG. 1, the surgeon may use a needle 20 having a cannula 22, and a handle 26. The handle 26 can be any size and shape so long as it provides a gripping surface to the surgeon. As illustrated in FIG. 1, the handle 26 can have two enlarged portions on either side of the cannula 22. In an aspect, the handle 26 can have a textured surface or can be honeycombed. The cannula 22 is a hollow tubular member that extends into the handle 26 at a proximal end of the needle 20. The cannula 22 is configured and dimensioned to receive the stylet 24 and a probe 40.

The system can also comprise a stylet 24. In an aspect, the stylet 24 can have at its distal end a beveled tip that extends into an elongated shaft that extends into an enlarged portion at its proximal end. The beveled tip of the stylet can be used to pierce the osseous tissue.

Figure 2A:
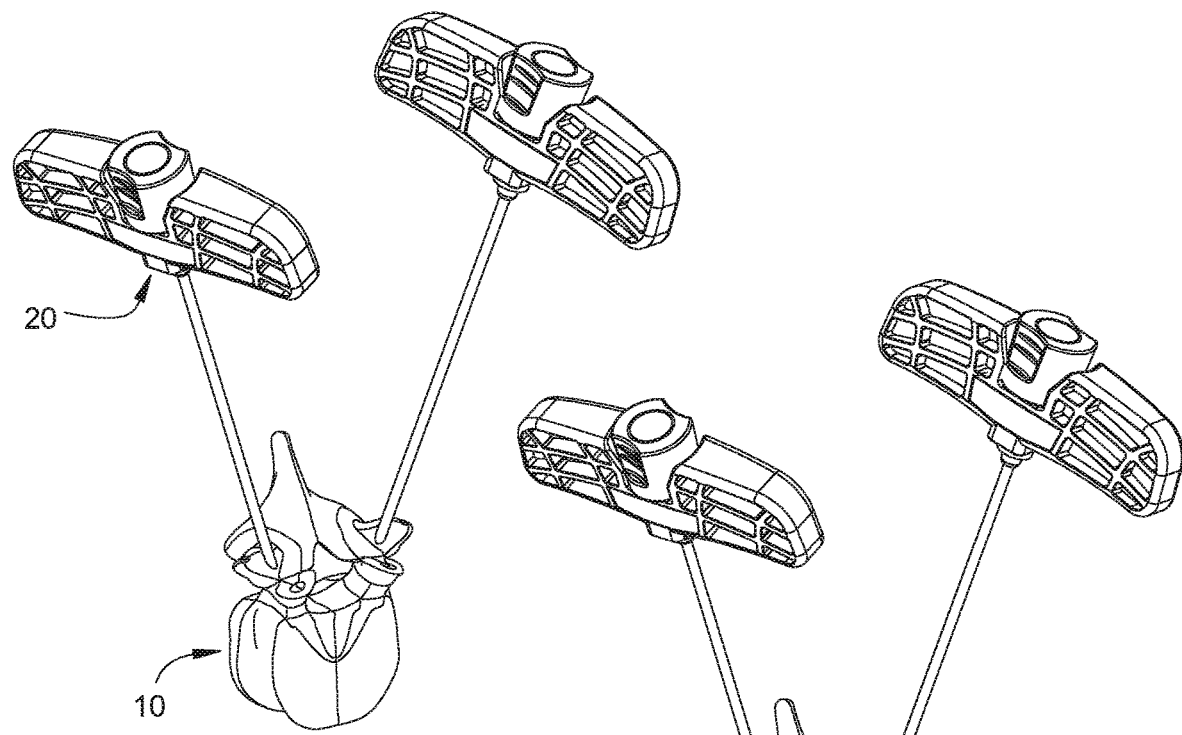
FIG. 2A is an isometric view of two needles inserted into a vertebral body.
Figure 2B:
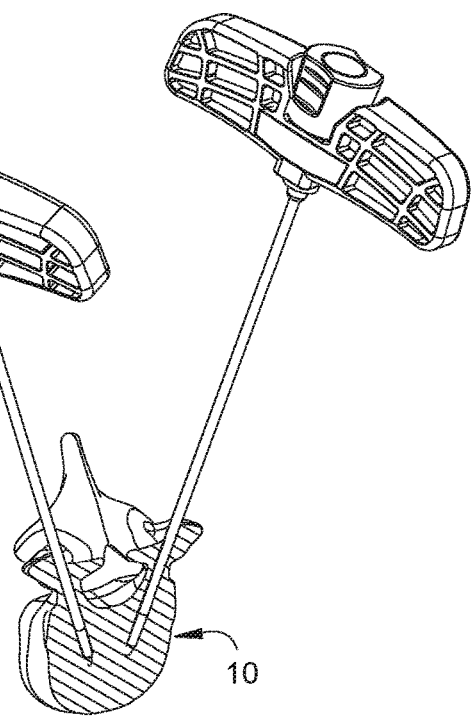
FIG. 2B is a section view of two needles inserted into the pedicles of the vertebral body.
Figure 2C:
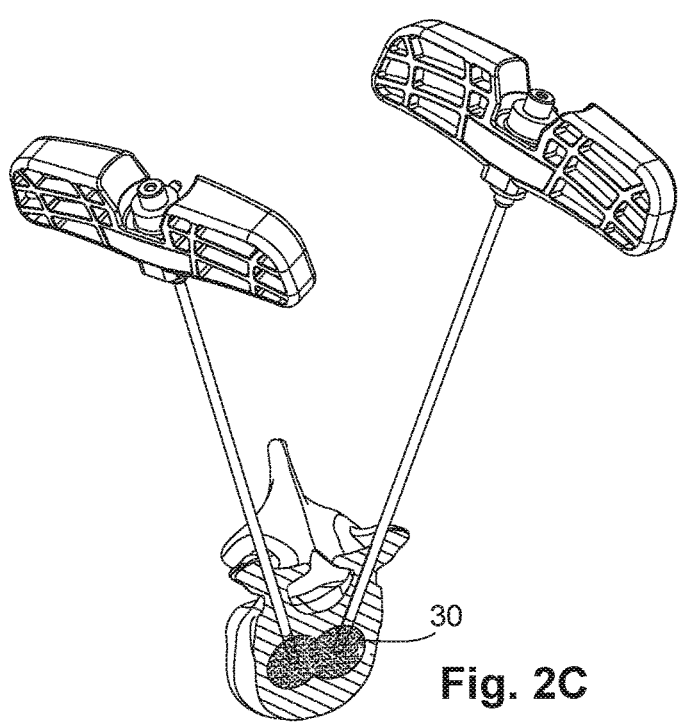
FIG. 2C is a section view of a bone lesion formed in the vertebral body.

The needle 20, with the stylet 24 inserted into the cannula 22, can be inserted into osseous tissue, such as a pedicle, of a vertebral body 10, as shown in the third image of FIG. 1. In an aspect, more than one needle 20 can be inserted into the osseous tissue of a vertebral body 10, as illustrated in FIG. 2A. Once the needle 20 has been inserted into the osseous tissue the stylet 24 can be removed, as shown in FIG. 2C. This allows for a pathway into the vertebral body 10 via the cannula 22 of the needle 20. In another aspect, two needles 20 can be used on one vertebral body as shown in FIGS. 2A-2C. If one or more needle 20 is used, they can be inserted simultaneously or consecutively. In another aspect, one needle 20 can be used on one vertebral body.

As shown in FIG. 2C, the cannula 22 can also serve as a conduit for the delivery of a fluid 30 into the vertebral body. In an aspect, the fluid 30 can be present in a syringe with a tube (not shown) that can be inserted into the cannula 22. In another aspect, the fluid 30 can be present in a holding container (not shown) having an external pump and tubing that can be inserted into the cannula 22. In addition, a separate tubing can be used to withdraw fluid 30 from the vertebral body. Additionally, a temperature controlling device can also be attached to the holding container to regulate the temperature of the fluid 30, i.e., heat or cool the fluid to a desired temperature. Any amount of fluid 30 can be inserted into the vertebral body 10 via the cannula 22.

The fluid 30 can be a hypertonic saline or other thermal transfer enhancement medium to uniformly deliver the energy of the probe 40 through the osseous tissue surrounding the insertion site. In an aspect, no fluid 30 is used in the method and instead a probe 40 can be used to deliver energy directly to the osseous tissue.

Figure 3:
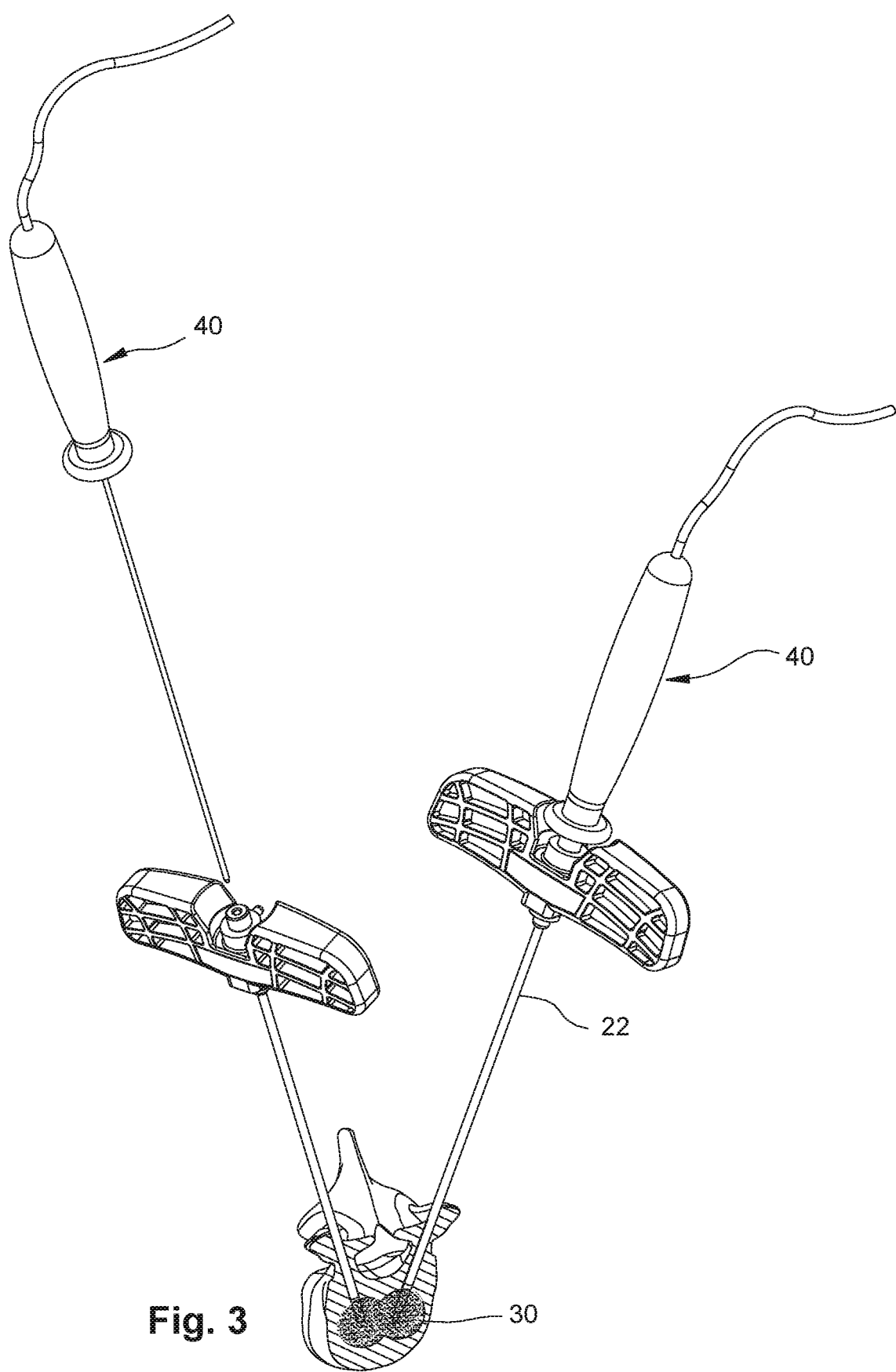
FIG. 3 is a section view of a probe inserted through the needle cannula and into the vertebral body.

After the fluid 30 has been inserted into the vertebral body 10, a probe 40 can be inserted into the cannula 22. As shown in FIG. 3, the cannula 22 can be configured and dimensioned to receive the probe 40. In an aspect, the probe 40 can be any device that emits energy to the fluid 30 and/or the osseous tissue surrounding the insertion site. For example, the probe 40 can emit radio frequency waves, microwaves, and ultrasonic waves. The probe 40 can be a radio frequency probe, a laser, a microwave energy probe, and an ultrasonic probe. A frequency range for the ultrasound can range from about 6 KHz to about 9 KHz, for example from about 6 KHz to about 8 KHz, and as a further example can be 7 KHz. The probe 40 applies an energy into the vertebral body 10 to ablate the osseous tissue.

The energy from the probe 40 applied to the fluid 30 and/or the osseous tissue can cause an increase in temperature of the fluid 30 and surrounding osseous tissue or can cause a decrease in temperature of the fluid 30 and surrounding osseous tissue. The user can determine whether a heat treatment or cold treatment would be effective for ablating the tissue and creating a higher density bone portion.

In the case of applying heat energy from the probe 40 the temperature should range from about 30° C. to about 60° C., for example from about 42° C. to about 50° C. When applying energy from the probe 40 for a cold treatment, the temperature should range from about −5° C. to about 25° C., for example from about 0° C. to about 20° C. A thermocouple can be attached to the probe 40 to measure the temperature.

In an aspect, a user could apply a heat treatment to the vertebral body followed by a cold treatment. In another aspect, the user could apply a cold treatment followed by a heat treatment. It is envisioned that any single treatment (heat or cold) and/or any combination of treatments could be applied so long as the osseous tissue is ablated.

The time of application of energy from the probe 40 can be inversely proportional to the desired temperature. For example, a desired temperature of about 42° C. can be maintained by applying energy from the probe 40 for about 2 hours to achieve the desired bone ablation. As another example, a desired temperature of about 50° C. can be maintained by applying energy from the probe 40 for about 1 minute to achieve a similar bone ablation. It is envisioned that energy from the probe 40 can be applied over a period of time ranging from about 1 minute to about 2 hours, depending upon the desired temperature, in order to achieve bone ablation.

Once the energy has been applied for the desired amount of time, the probe 40 can be removed from the cannula 22. The ablated osseous tissue will fill with blood and eventually turn into bone with a denser ring of bone appearing on the perimeter of the ablated osseous tissue thereby creating a higher density bony portion. It is this increased bone density that is desired as this can allow the vertebral body 10 to withstand a higher load than that previous to the treatment. The treated vertebral body 10 will now be able to offset some of the loading on the instrumented levels and transition the loading on the spine and may reduce the incidence of PJK at these adjacent levels. In an aspect, the disclosed method can be performed at the same time as a spinal procedure directed to instrumented levels or it can be performed hours, days, or weeks before in order to allow the vertebral body 10 to form the higher density bony portion.

Figure 4A:
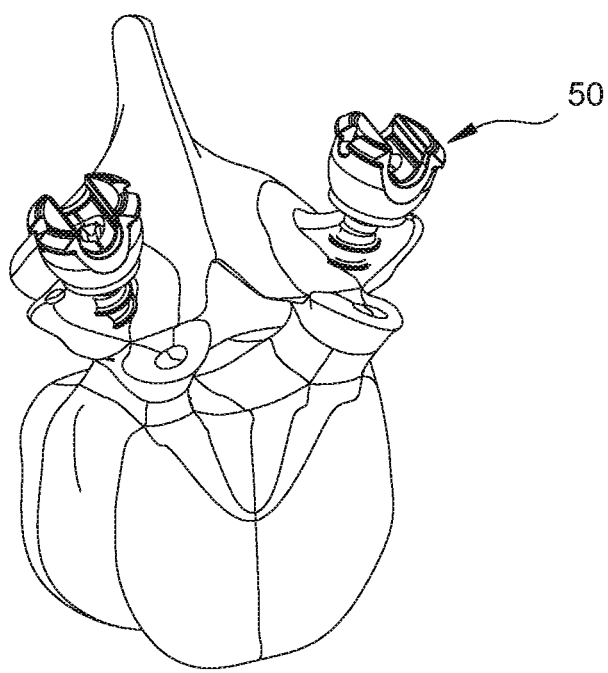
FIG. 4A is an isometric view of pedicle screws inserted into a vertebrae.
Figure 4B:
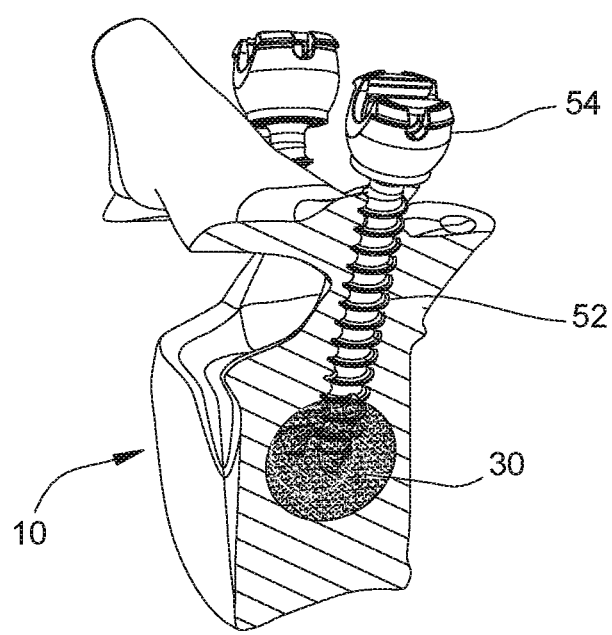
FIG. 4B is a section view of FIG. 4A with the presence of a lesion formed in the vertebra body.

In another aspect, the method can comprise inserting a needle 20 with the stylet 24 into a vertebral body 10. The needle 20 and stylet 24 can then be removed from the insertion site. The user can insert a screw 50, such as a pedicle screw, into the insertion site, as shown in FIG. 4A. The screw 50 can have a head portion 54 and a shank portion 52, as shown in FIG. 4B. The screw 50 can also have a cannula (not shown) or have fenestrations along the length of its shank portion 52. The cannula and/or fenestrations present in the screw 50 can be a conduit for introducing a fluid 30 into the vertebral body 10. The cannula of the screw 50 can also act as the conduit for the probe 40. The screw 50 itself can also conduct the energy of the probe 40 and can allow for bone densification along its length and into the pedicle of the vertebral body 10.

As with the previously described aspect, the fluid 30, the screw 50, and/or the osseous tissue surrounding the insertion site of the screw 50 can be heated or cooled to a desired temperature over a period of time in order to ablate the osseous tissue. As previously described, the ablated tissue will then be converted into a higher density bony portion. Once this higher density bony portion is achieved, the screw 50 can stay in place or be removed by the surgeon.

It is envisioned in both aspects, that the described method can cause a regrowth of the osseous tissue in response to the ablation such that the bone density is greater than that of the untreated osseous tissue. This can be achieved by various combinations of the above-mentioned treatment temperatures and times. It should be considered that some treatment modalities can be more suited to treating the cortical shell of the vertebra while others can be better suited to treating the cancellous portion of the vertebra. Thus a dual treatment modality can be appropriate in some cases. The higher density bone portion can provide a transition of spinal loading from the instrumented level to the un-instrumented level(s).

In some aspects, multiple levels of vertebral body 10 can be treated in varying amounts of ablation. For example, a higher density bone portion can be used in one or more adjacent levels in varying amounts of ablation so that there is a tapering amount of higher density bone portion formed in each subsequent vertebral level. This tapering of higher density bone portion can be used at the cranial end to facilitate reducing the stress impact on the cranial, non-instrumented adjacent level(s) to the spinal construct. In another aspect, should the caudal level require this load transitioning, the ablation treatments can be used at the adjacent caudal levels as well. Subsequently, both the cranial and caudal adjacent level(s) can be treated in one construct should this be desired.

This type of ablation treatment can also be applicable to forms of bone or spinal diseases including osteopenia or osteoporosis. The levels of vertebral bodies to be instrumented can also be treated by the disclosed method prior to placement of instrumentation or at the time of instrumentation.

There is also disclosed a kit for ablating a vertebral body. The kit can comprise a screw having a cannula and fenestrations; and at least one probe. The kit can also comprise a needle having a handle and a cannula; and a stylet.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A method for ablating osseous tissue in a vertebra, the method comprising:
    providing an ablation system including:
        a needle including:
            a handle disposed at a proximal portion thereof; and
            a first cannula coupled to the handle and extending distally therefrom;
        a stylet configured to be advanced within the first cannula;
        a screw including a second cannula, the screw configured to be received within the vertebra; and
        a probe sized to fit within the second cannula of the screw, the probe having energy emission characteristics tailored for increasing a density of the osseous tissue;
    advancing the needle and the stylet into the osseous tissue of a body of the vertebra;
    removing the needle and the stylet from the osseous tissue;
    advancing the screw into the osseous tissue in the body of the vertebra along a path of the needle such that the screw is disposed in a pedicle and the body;
    advancing the probe through the second cannula of the screw such that the probe is positioned through a length of the screw; and
    while the probe is positioned through the length of the screw, applying energy from the probe such that the screw conducts the energy and a density of the pedicle and the osseous tissue of the body increases.

2. The method of claim 1, wherein the first cannula defines a hollow tubular member that extends into the handle at the proximal portion of the needle.

3. The method of claim 1, wherein advancing the probe involves advancing a probe selected from the group consisting of:
    a radio frequency probe, a microwave energy probe, a fluid probe, and an ultrasonic probe.

4. The method of claim 1, further including removing the stylet from the needle before removing the needle from the osseous tissue.

5. The method of claim 1, wherein providing the screw further comprises providing the screw including at least one fenestration therein.

6. The method of claim 5, further including injecting a fluid having thermal transfer enhancement properties into the needle and through the screw such that the fluid is received within the osseous tissue.

7. The method of claim 1, further including introducing a fluid having thermal transfer enhancement properties through the needle and into the osseous tissue.

8. The method of claim 1, further including introducing a fluid having thermal transfer enhancement properties through the screw and into the osseous tissue.

9. The method of claim 1, wherein applying energy from the probe involves applying energy selected from the group consisting of: radio frequency waves, microwave energy, and ultrasonic waves.

10. The method of claim 1, wherein the probe applies energy to the osseous tissue to raise a temperature of the osseous tissue.

11. The method of claim 10, wherein the probe applies energy to the osseous tissue to raise the temperature of the osseous tissue to between about 30° C. to about 60° C.

12. The method of claim 1, wherein the probe applies energy to the osseous tissue to lower a temperature of the osseous tissue.

13. The method of claim 12, wherein the probe applies energy to the osseous tissue to lower the temperature of the osseous tissue to between about −5° C. to about 24° C.

14. The method of claim 1, wherein the probe applies energy to the osseous tissue for a period of time ranging from about 1 minute to about 2 hours.

15. The method of claim 1, wherein advancing the screw into the osseous tissue involves advancing the screw into a portion of the osseous tissue in a diseased condition.

16. The method of claim 1, wherein the probe is an ultrasonic probe with a frequency within a range from about 6 KHz to about 9 KHz.

17. A method of ablating osseous tissue in a plurality of vertebral bodies, the method comprising:
   identifying a first location within a first osseous tissue region of a first vertebral body;
   advancing a needle into the first osseous tissue region;
   advancing a probe into a cannula of the needle such that the probe is received within the first osseous tissue region at the first location;
   while the probe is disposed at the first location, applying energy from the probe into the first osseous tissue region to ablate a first volume of osseous tissue at the first location in a manner such that a density of the first volume of osseous tissue increases;
   identifying a second vertebral body immediately adjacent to the first vertebral body such that a single disc space separates the second vertebral body from the first vertebral body;
   identifying a second location within a second osseous tissue region of the second vertebral body;
   advancing the needle into the second osseous tissue region;
   advancing the probe into the cannula of the needle such that the probe is received within the second osseous tissue region at the second location;
   while the probe is disposed at the second location, applying energy from the probe into the second osseous tissue region to ablate a second volume of osseous tissue at the second location in a manner such that a density of the second volume of osseous tissue increases;
   identifying a third vertebral body immediately adjacent to the second vertebral body such that a single disc space separates the third vertebral body from the second vertebral body;
   identifying a third location within a third osseous tissue region of the third vertebral body;
   advancing the needle into the third osseous tissue region;
   advancing the probe into the cannula of the needle such that the probe is received within the third osseous tissue region at the third location; and
   while the probe is disposed at the third location, applying energy from the probe into the third osseous tissue region to ablate a third volume of osseous tissue at the third location in a manner such that a density of the third volume of osseous tissue increases,
   wherein the first volume of osseous tissue is greater than the second volume of osseous tissue and the second volume of osseous tissue is greater than the third volume of osseous tissue.

18. The method of claim 17, wherein advancing the probe into the first osseous tissue region involves advancing a probe selected from the group consisting of: a radio frequency probe, a microwave energy probe, a fluid probe, and an ultrasonic probe.

19. The method of claim 17, wherein advancing the probe into the first osseous tissue region involves advancing an ultrasonic probe with a frequency within a range from about 6 KHz to about 9 KHz.

20. The method of claim 17, further comprising introducing a fluid having thermal transfer enhancement properties through the cannula of the needle and into the first osseous tissue region prior to advancing the probe to the first location.

21. The method of claim 17, wherein applying energy from the probe into the first osseous tissue region raises a temperature of at least a portion of the first osseous tissue region.

22. The method of claim 17, wherein applying energy from the probe into the first osseous tissue region raises a temperature of at least a portion of the first osseous tissue region to between about 30° C. to about 60° C.

23. The method of claim 17, wherein applying energy from the probe into the first osseous tissue region lowers a temperature of at least a portion of the first osseous tissue region.

24. The method of claim 17, wherein applying energy from the probe into the first osseous tissue region lowers a temperature of at least a portion of the first osseous tissue region to between about −5° C. to about 24° C.

25. The method of claim 17, wherein the probe applies energy into the first osseous tissue region for a period of time ranging from about 1 minute to about 2 hours.

26. The method of claim 17, wherein identifying the first location within the first osseous tissue region involves identifying a portion of the first osseous tissue region in a diseased condition.

* * * * *